United States Patent
Zoughi et al.

(10) Patent No.: US 7,439,749 B2
(45) Date of Patent: Oct. 21, 2008

(54) NON-DESTRUCTIVE TESTING OF PHYSICAL CHARACTERISTICS OF COMPOSITE STRUCTURES

(75) Inventors: Reza Zoughi, Wildwood, MO (US); Sergiy Kharkivskiy, Rolla, MO (US); Vivian Stephen, Annandale, VA (US)

(73) Assignee: The Curators of the University of Missouri, Rolla, MO (US)

( * ) Notice: Subject to any disclaimer, the term of this patent is extended or adjusted under 35 U.S.C. 154(b) by 0 days.

(21) Appl. No.: 11/551,800

(22) Filed: Oct. 23, 2006

(65) Prior Publication Data

US 2008/0129316 A1 Jun. 5, 2008

(51) Int. Cl.
G01R 27/04 (2006.01)
G01R 27/32 (2006.01)
(52) U.S. Cl. ...................... 324/637; 324/644
(58) Field of Classification Search ................ 324/637, 324/629, 600, 500, 512, 528, 531, 555, 718, 324/456, 216, 237, 238, 240
See application file for complete search history.

(56) References Cited

U.S. PATENT DOCUMENTS

| | | | | |
|---|---|---|---|---|
| 4,627,998 | A * | 12/1986 | Akihama et al. | 428/294.7 |
| 5,617,685 | A * | 4/1997 | Meier et al. | 52/223.8 |
| 5,886,534 | A | 3/1999 | Bakhtiari et al. | |
| 5,905,380 | A * | 5/1999 | Weiner et al. | 324/644 |
| 6,359,446 | B1 | 3/2002 | Little, Jr. | |
| 6,429,802 | B1 * | 8/2002 | Roberts | 342/22 |
| 6,462,561 | B1 | 10/2002 | Bigelow et al. | |
| 6,674,292 | B2 | 1/2004 | Bray et al. | |
| 7,075,315 | B2 * | 7/2006 | Tanaka | 324/642 |
| 7,295,152 | B2 * | 11/2007 | Shima | 342/174 |
| 2004/0239345 | A1 * | 12/2004 | Amini | 324/702 |
| 2005/0076596 | A1 * | 4/2005 | Igarashi | 52/514 |
| 2006/0102345 | A1 * | 5/2006 | McCarthy et al. | 166/250.1 |

OTHER PUBLICATIONS

S. Kharkovsky, A.C. Ryley, V. Stephen and R. Zoughi, "Dual-Polarized Microwave Near-Field Reflectometer for Non-Invasive Inspection of Carbon Fiber Reinforced Polymer (CFRP) Strengthened Structures," Proc. of the IEEE Instrumentation and Measurement Technology Conference, pp. 2108-2111 (p. 1-4), Sorrento, Italy, Apr. 24, 2006.

Y. Kim, et al.; Microwave-Based NDE of FRP-Jacketed Concrete Structures; Presented May 6, 2001 at Proceedings of SAMPE, Long Beach, California, 12 pages.

International Search Report, PCT/US07/82192, dated Apr. 30, 2008, 2 pages.

Written Opinion, PCT/US07/82192, dated Apr. 30, 2008, 7 pages.

\* cited by examiner

*Primary Examiner*—Vincent Q. Nguyen
*Assistant Examiner*—Hoai-An D Nguyen
(74) *Attorney, Agent, or Firm*—Senniger Powers LLP

(57) ABSTRACT

A method for detecting an anomaly in a composite material comprising directing two transmitted electromagnetic wave signals orthogonally polarized with respect to each other from a probe to the composite material, wherein the probe and composite material are positioned for near-field evaluation of the probe. A related apparatus comprising an open-ended square waveguide probe.

22 Claims, 21 Drawing Sheets

NON-DESTRUCTIVE TESTING OF PHYSICAL CHARACTERISTICS OF COMPOSITE STRUCTURES

FIELD OF THE INVENTION

This invention is directed to a method and apparatus for nondestructive testing and evaluation of composite structures, such as complex fibrous structural materials.

BACKGROUND OF THE INVENTION

Composite structures comprising fibers in a matrix material have received increased attention in recent years for a wide variety of applications including commercial, civil, industrial, military, and other applications. For example, carbon fiber reinforced polymer (CFRP) materials are increasingly being used for structural applications, such as rehabilitation and upgrade of concrete structures. The invention encompasses testing of any materials comprising aligned elements such as fibers in a dielectric matrix, and is described herein with emphasis on CFRP materials for illustration purposes only.

Carbon fiber reinforced polymer materials have unidirectional carbon fibers impregnated with epoxy. Such composites are externally bonded to concrete members to provide supplemental flexural, shear, or confining reinforcement. Proper adhesion of the CFRP material to the concrete structure can be critical to achieving the desired transfer of stresses to the CFRP material. However, disbond between the CFRP material and the concrete can occur due to, for example, improper application, moisture, or impact damage. Similarly, delamination within the CFRP material can interfere with internal distribution of stresses and overall performance.

Damage to concrete (for instance, impact damage) under CFRP laminates can be also critical to providing the engineering properties for which CFRP laminates are being employed because the damages of concrete under CFRP laminates are not visible through the CFRP.

Heretofore, nondestructive testing techniques have not always been effective for testing composites for conditions such as disbanding, delamination, and damage to concrete under CFRP. Microwave techniques have been employed whereby microwaves are directed at a specimen, and reflected microwaves signals are evaluated for changes indicative of anomalies in the specimen which may be indicative of defects. Standoff distance—distance between the specimen surface and the signal sensor—often changes while scanning a specimen due to local relative tilt of the specimen surface, shaking or movement of the specimen or the probe, specimen roughness, bulging, or other reasons. These changes can significantly influence the properties of the reflected microwave signal. Subtle anomalies such as disbonds and delaminations can be easily masked by standoff distance change influences.

U.S. Pat. No. 6,359,446 discloses nondestructive testing of dielectric materials using monochromatic, phase coherent electromagnetic radiation, preferably in the 5 to 50 GHz range (microwave range). A portion of the impinged beam is combined with the signal reflected by the test specimen. The signals combine to produce an interference pattern. The measurements are sensitive to variations in standoff distance.

One method which has been attempted to address the standoff distance issue has been the use of a mechanical system such as rollers that maintain the standoff distance fairly constant during the scan. However, this method is ineffective when the specimen has local surface roughness/bulging that may be smaller in spatial extent than the inspection area of the open-ended probe. Moreover, this requires contact between a component of the test device and the specimen.

Another attempted method involves measuring standoff distance variation during the scan and then subsequently processing the data to subtract the effect of standoff distance variation from the reflected signal. In particular, U.S. Pat. No. 6,462,561 discloses a near-field sensor including circuitry which compensates for variations in standoff distance. The method by which standoff distance is removed as an influence, however, requires that there be contact between a component of the test device and the specimen; so the method is not "non-contact." In particular, it employs a potentiometer distinct from the waveguide probe. This can render the technique inoperable for certain applications where access to the object surface is limited by the placement of the object or its shape. Also, its accuracy is limited by the fact that the potentiometer and waveguide probe, being distinct components, are not taking measurements simultaneously from the same location.

In another method a differential sensing system is used to subtract out of the vibrational signals or noise as disclosed in an alternative aspect of U.S. Pat. No. 5,886,534. Instead of a single antenna and reflector arrangement in the original millimeter wave system 10 for on-line inspection of thin sheet dielectrics, a dual arrangement of a pair cross polarized antennas 34A and 34B and corresponding dual reflectors 16' is provided in the alternative, differential sensing system 10' as shown in FIG. 6 of this patent. The separation between the two sensing locations is provided such that there is no coupling or interference between two signals of the antennas. Because of close proximity, for example, about 3 inches, vibrational signal levels are expected to be identical at two locations. Consequently, if a difference of the two sensor signals is obtained the vibrational signals or noise are subtracted by a differencing scheme consists of a millimeter wave hybrid coupler 92 and a differential detector 96. If, on other hand, oriented defects such as warp or picks defects lay in the field of view of both antennas, the deferential sensing would give a defect-related signal because one sensor will be more sensitive that the other, depending on the defect orientation. This method and system provides inspection of thin sheet dielectrics with removal of influence of standoff distance variation caused by the vibration of the sheet. However, this method is ineffective when the specimen has surface roughness/bulging that may be smaller in spatial extent than the separation between the two sensing locations (about 3 inches) or when defects are not oriented. Moreover, this method and system provides only simple subtraction of two cross-polarized reflected signals that can be useful in limited applications because interaction of the cross-polarized signals with the specimen can be different.

SUMMARY OF THE INVENTION

Briefly, therefore, the invention is directed a method for detecting an anomaly in a composite material comprising directing two transmitted electromagnetic wave signals orthogonally polarized with respect to each other from a probe to the composite material, wherein the probe and composite material are positioned for near-field evaluation of the probe; receiving two reflected signals corresponding to said two transmitted orthogonally polarized signals; and issuing information about the composite material developed as a function of the two reflected signals.

The invention is also directed to a method for detecting an anomaly in a composite material comprising directing two transmitted electromagnetic wave signals from a probe to the composite material, wherein the two transmitted electromagnetic wave signals are orthogonally polarized with respect to each other and are issued at respective frequencies different from each other; receiving two reflected signals corresponding to said two transmitted electromagnetic wave signals which are orthogonally polarized; and issuing information about the composite material developed as a function of the two reflected signals.

In another aspect the invention is directed to a method for detecting an anomaly in a carbon fiber reinforced polymer material adhered to a concrete substrate comprising directing two transmitted electromagnetic wave signals from a probe to the carbon fiber reinforced polymer material, wherein a first of the two transmitted electromagnetic wave signals is polarized parallel to the preferred orientation of carbon fibers in the carbon fiber reinforced polymer material, and a second of the two transmitted electromagnetic wave signals is polarized orthogonally with respect to the first of the signals; receiving two reflected signals corresponding to said two transmitted electromagnetic signals which are orthogonally polarized; and issuing information about the composite material developed as a function of the two reflected signals.

A further aspect of the invention is an apparatus for detecting an anomaly in a composite material comprising fibers within a dielectric material, the apparatus comprising a probe comprising a first transmitter for transmitting electromagnetic signals with a first electric field polarization vector orientation at the composite material located in near-field region of the probe, and a second transmitter for transmitting electromagnetic wave signals with a second electric field polarization vector orientation at the composite material, wherein the second electric field polarization vector orientation is orthogonal to the first electric field polarization vector orientation; the probe further comprising a first receiver for receiving reflected signals of the first polarization orientation, and a second receiver for receiving reflected signals of the second polarization orientation; and a conditioning circuit for translating the reflected signals to information about the composite material.

Other objects and features of the invention will be in part apparent and in part pointed out herein.

DETAILED DESCRIPTION OF PREFERRED EMBODIMENTS

Figure 1:
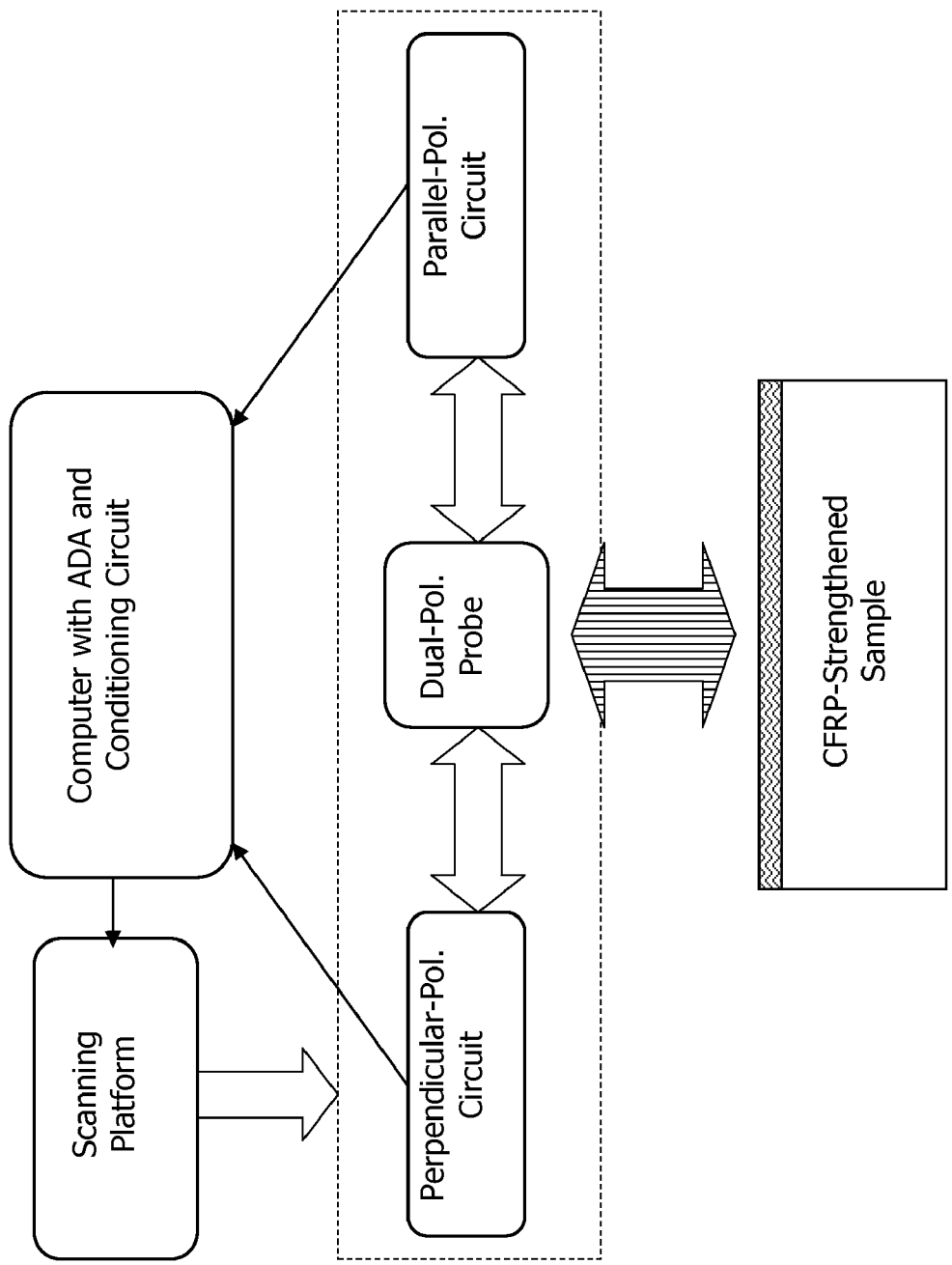
FIG. 1 is a schematic representation of the testing apparatus of the invention.

The present invention in one aspect employs two electromagnetic wave signals such as microwave or millimeter wave signals which are orthogonal to each other, in a near-field region of one radiator (sensor). These signals react differently when directed at materials containing certain aligned features. That is, for a material containing elongate elements aligned in a generally common direction within a dielectric matrix, electromagnetic waves of a polarization substantially parallel to the common direction of the elongate features reflect off the elongate features and do not penetrate the material. And electromagnetic waves of a polarization substantially perpendicular to the common direction of the elongate features do not reflect off the elongate features; rather they travel past the elongate materials and penetrate the dielectric. For example, where the specimen is carbon fiber reinforced polymer (CFRP) with the carbon fibers in unidirectional alignment, electromagnetic waves of a polarization which is parallel to the fiber alignment reflect off the carbon fibers and do not penetrate the material. That is, when the fiber directions and the signal electric field polarization vector are parallel to one another, the signal reflects off the surface of the material, resulting in very little signal penetration. The reflected signal of parallel polarization, therefore, is affected essentially only by standoff distance, and is not affected by any characteristics below the specimen surface. In contrast, electromagnetic waves of a polarization perpendicular to the fiber alignment penetrate the material. That is, when the electromagnetic wave signal polarization vector is perpendicular to the fiber direction the CFRP material is essentially a dielectric sheet: the signal penetrates through it and can detect the presence of a subsurface anomaly such as a disbond between CFRP sheet and substrate (concrete). That is, the perpendicular signal penetrates through the CFRP and reflects off whatever is behind it, such as concrete. While the perpendicular-polarized signal penetrates through the material, is reflected off the underlying substrate, and penetrates back through the material to the detector, its characteristics as detected are affected by any disbond or delamination, and they are affected by any standoff distance. The invention therefore employs the parallel-polarized signals and the perpendicular-polarized signals to generate a composite signal reflecting characteristics with influence of standoff distance removed. The parallel-polarized reflected signal which is sensitive to the standoff distance is used to remove the influence of changing standoff distance from the perpendicularly-polarized reflected signal. It can be also used for monitoring of standoff distance variation or surface roughness.

Carbon fiber reinforced polymer materials are appropriate for testing with this invention. Other materials comprising elongate elements which are electrically conductive or which reflect electromagnetic radiation in a dielectric matrix are also appropriate. The materials, therefore, manifest an isotropic surface. Examples of such materials include reinforcing metal wires or strands in dielectric. The specific nature of these materials is not critical, provided they contain elongate elements of a generally common alignment in a dielectric matrix and the elongate elements reflect electromagnetic radiation. Stated another way, the specific nature of the materials is not critical, provided that of impinging orthogonal waves, one set is substantially penetrating and one set is substantially not penetrating.

In practical application the preferred embodiment of the invention employs a dual-polarized near-field open-ended waveguide probe that simultaneously transmits and receives the two orthogonally polarized microwave signals. The preferred embodiment of the invention employs an open-ended square waveguide probe. The sides of the opening are all four of equal length. With two distinct transmitters inside the probe, it transmits two orthogonally polarized signals.

In one aspect the invention is directed to an inspection apparatus comprising a number of components, including a reflectometer with an open-ended waveguide probe. A preferred embodiment shown schematically in FIG. 1 has the dual-polarized microwave waveguide probe introduced above for directing microwaves at a specimen under inspection and receiving microwaves reflected from the specimen. There are a parallel-polarization circuit and a perpendicular-polarization circuit for the two microwave signals of the dual-polarized system. There is a computer-controlled two-dimensional scanning mechanism such as a computerized scanning platform for achieving relative movement between the probe and the specimen. A conditioning circuit compensates for variations in the standoff distance between the probe and the specimen surface.

Figure 2:
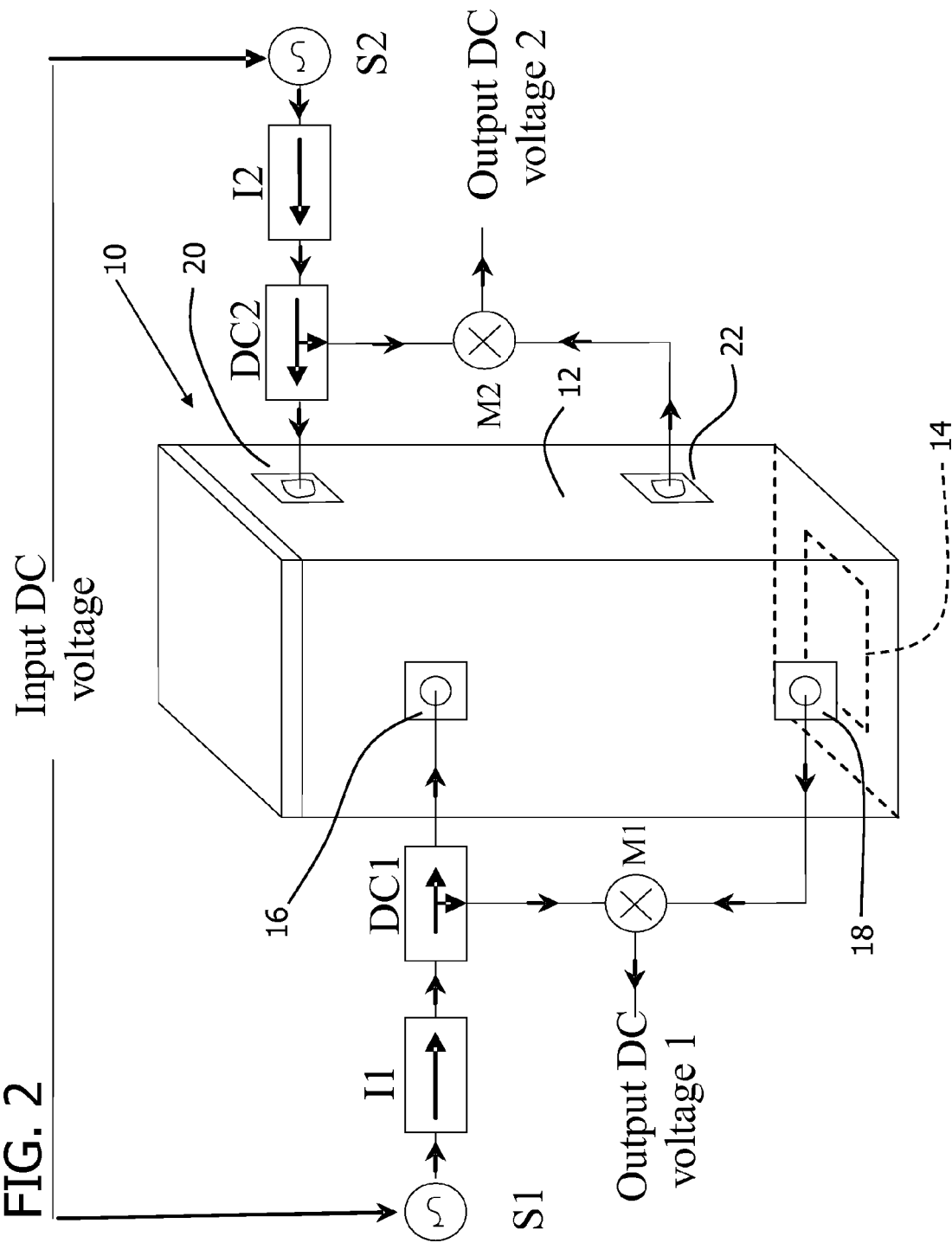
FIG. 2 is schematic representation of the dual-polarized square waveguide and accompanying circuitry employed as a component of the invention.

The dual-polarized waveguide 10 shown in FIG. 2 comprises a housing 12 and an opening 14 to be directed toward the specimen being inspected. There is a first microwave circuit for microwave signals with polarization perpendicular to the orientation of the relevant feature of the specimen and a second microwave circuit for microwave signals with polarization parallel to the orientation of the relevant feature of the specimen. The first and second circuits comprise a microwave source (S1, S2), an isolator (I1, I2), a directional coupler (DC1, DC2), and a mixer (M1, M2).

The first circuit has a port 16 in communication with a first transmitter and a port 18 in communication with a first receiver. The first transmitter is inside the housing and transmits microwaves of perpendicular orientation through opening 14. The first receiver is inside the housing and receives microwave signals of perpendicular polarization which have reflected off the specimen and returned through the opening. The second circuit has a port 20 in communication with a second transmitter and a port 22 in communication with a second receiver. The second transmitter is inside the housing and transmits microwave signals of parallel polarization through opening 14. The second receiver is inside the housing and receives microwaves of parallel orientation which have reflected off the specimen and returned through the opening. The transmitter and receiver ports of the first circuit (e.g., the perpendicular circuit) are on a side of the waveguide probe which is orthogonal to the side on which the second circuit ports are, i.e., the ports for the parallel circuit. The relative locations of the transmitting and receiving ports and the lengths of the respective feed elements inside the waveguide are selected to minimize unwanted coupling and to increase internal isolation between the respective orthogonal polarized ports. For example, the location of the parallel-polarization signal receiver is selected so it intrudes into the waveguide probe housing at a location where the transmitted perpendicular polarized signal is at its minimum. The respected locations are selected by trial to achieve the highest level of isolation.

For further isolation between the two, in one embodiment of the invention the perpendicular- and parallel-polarized signals may be operated at different frequencies. For example, Table 1 illustrates data in one preferred embodiment of the dual-polarized reflectometer system designed at X-band (8.2-12.4 GHz). It can be seen from Table 1 that operating the perpendicular polarization port at 12.2 GHz and the parallel polarization port at 8.6 GHz yielded coupled signals of relatively weak (e.g., <−20 dBm) power (−29.9 and −24 dBm). Operating these ports at 11.6 GHz and 9.6 GHz advantageously yielded even weaker (e.g., <−30 dBm) power (−40 and −31.5 dB) coupled signals. In a preferred embodiment, therefore, the frequencies differ by at least about 2 GHz.

TABLE 1

| Frequency, GHz | | Power of desired signal, dBm | | Power of coupled signal, dBm | |
|---|---|---|---|---|---|
| Port 1 | Port 2 | Port 1 | Port 2 | Port 1 | Port 2 |
| 12.2 | | −16.6 | | | −29.9 |
| 11.6 | | −9.0 | | | −40 |
| | 8.6 | | −16.8 | −24 | |
| | 9.6 | | −9.6 | −31.5 | |

In contrast, results when the two ports are operated at the same frequency showed a relatively strong (>−10 dBm) unwanted coupled signal. Accordingly, in one preferred embodiment the dual-polarized reflectometer system is designed at two different frequencies, $f_1$=11.6 GHz and $f_2$=9.6 GHz.

The open-ended square configuration of the waveguide probe advantageously ensures that the two signals operate in their dominant $TE_{10}$ mode. This is advantageous because the waveguide probe configuration provides that the parallel and perpendicular polarized signals irradiate the same location on the specimen being evaluated with a relatively uniform electromagnetic field distribution for the two signals. This is important to ensure that the standoff compensation resulting from the received parallel-polarized signal corresponds to the same location at the surface of the specimen as does the received perpendicular-polarized signal which is being conditioned. The "same location" means that the irradiated areas are very similar for both parallel and perpendicular polarized signals due to the fact that at near field of the probe, the irradiated area is determined by the probe aperture dimensions. The aperture dimension of the square waveguide probe is the same for both polarizations, and the respective signals are both simultaneously issued from the same square waveguide probe. For example, the aperture dimension of the square waveguide probe in one embodiment at X-band of the invention is 23×23 mm, or 529 mm$^2$, so for illustration purposes, "same location" in the context of this embodiment is within 529 mm$^2$ of each other.

For each polarization—parallel and perpendicular—portions of the transmitted and reflected signals are combined in the mixer M1, M2 to produce DC output voltages primarily proportional to the phase difference between the transmitted signal and the received signal. The invention therefore preferably relies on differences in phase between the transmitted signal and the received signal. Alternatively, however, images could be produced based on differences in magnitude of the two signals, or based on both differences in phase and magnitude. Consequently, different circuits can be used to produce the DC voltages as described hereinbelow after the working examples. The output DC voltages are directed to the computer with analog-digital adapter, conditioning/compensator circuit, which makes the compensation discussed below, and display. The images which manifest different colors and/or intensities for different voltages are generated on the display.

The open-ended square waveguide probe shown in FIG. 2 is hollow. In an alternative embodiment, the waveguide probe is filled with a dielectric material such as Teflon. Filling the probe with dielectric effectively reduces the size of the probing aperture, which increases spatial resolution so smaller defects can be detected with higher resolution, if desired.

In a further alternative embodiment, an open-ended circular waveguide probe can be used, with proper orthogonal polarization of the respective signals.

Figure 3:
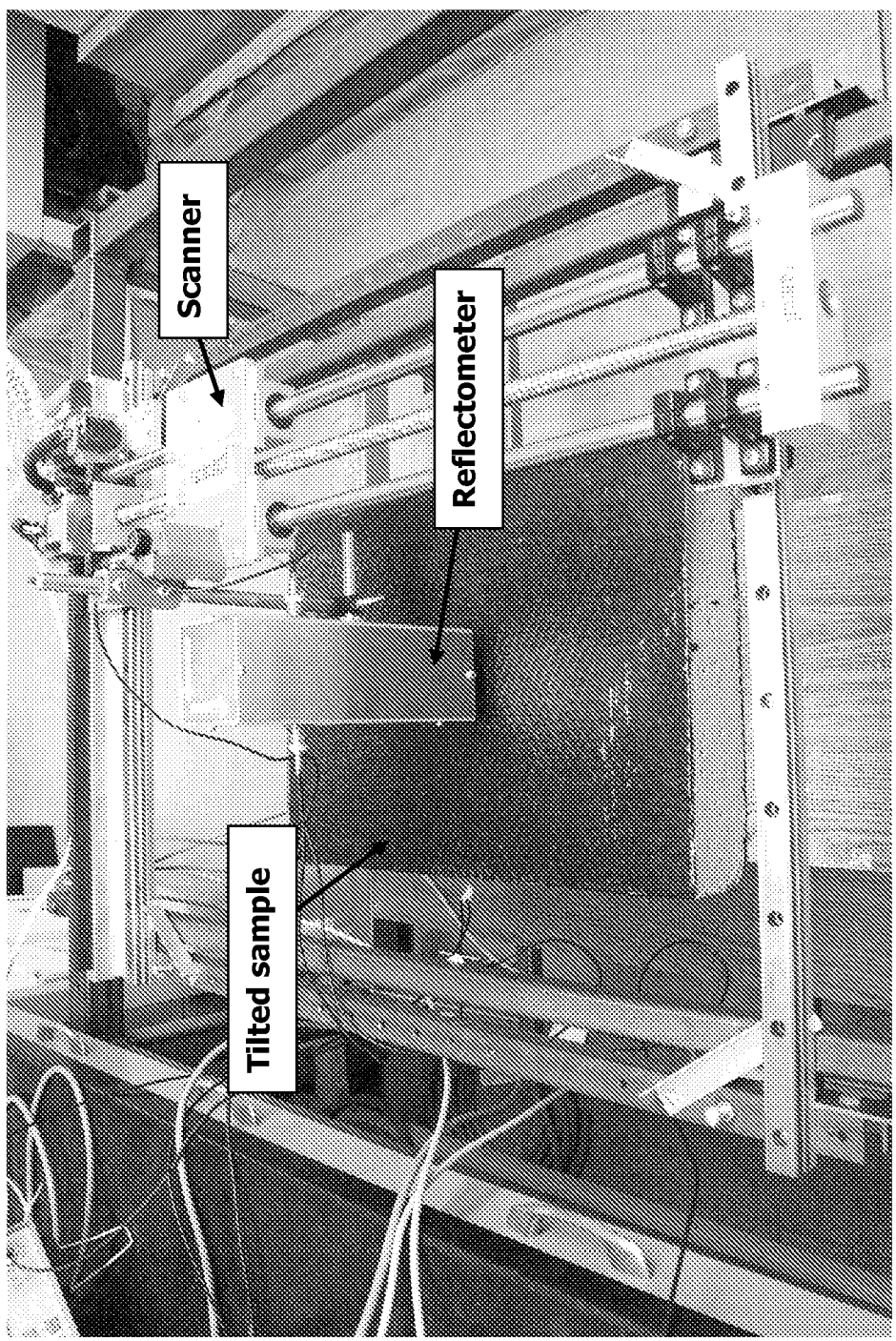
FIG. 3 is photograph of an embodiment of the testing apparatus of the invention.

One configuration of the apparatus of FIG. 1 in practical application is depicted in FIG. 3, with the sample (specimen), reflectometer, and scanner which mechanically moves the reflectometer with open-ended waveguide probe in x and y directions pointed out. The scanner moves the probe across the specimen taking data until the entire surface has been examined. The specimen depicted here is CFRP laminated to concrete.

Figure 4:
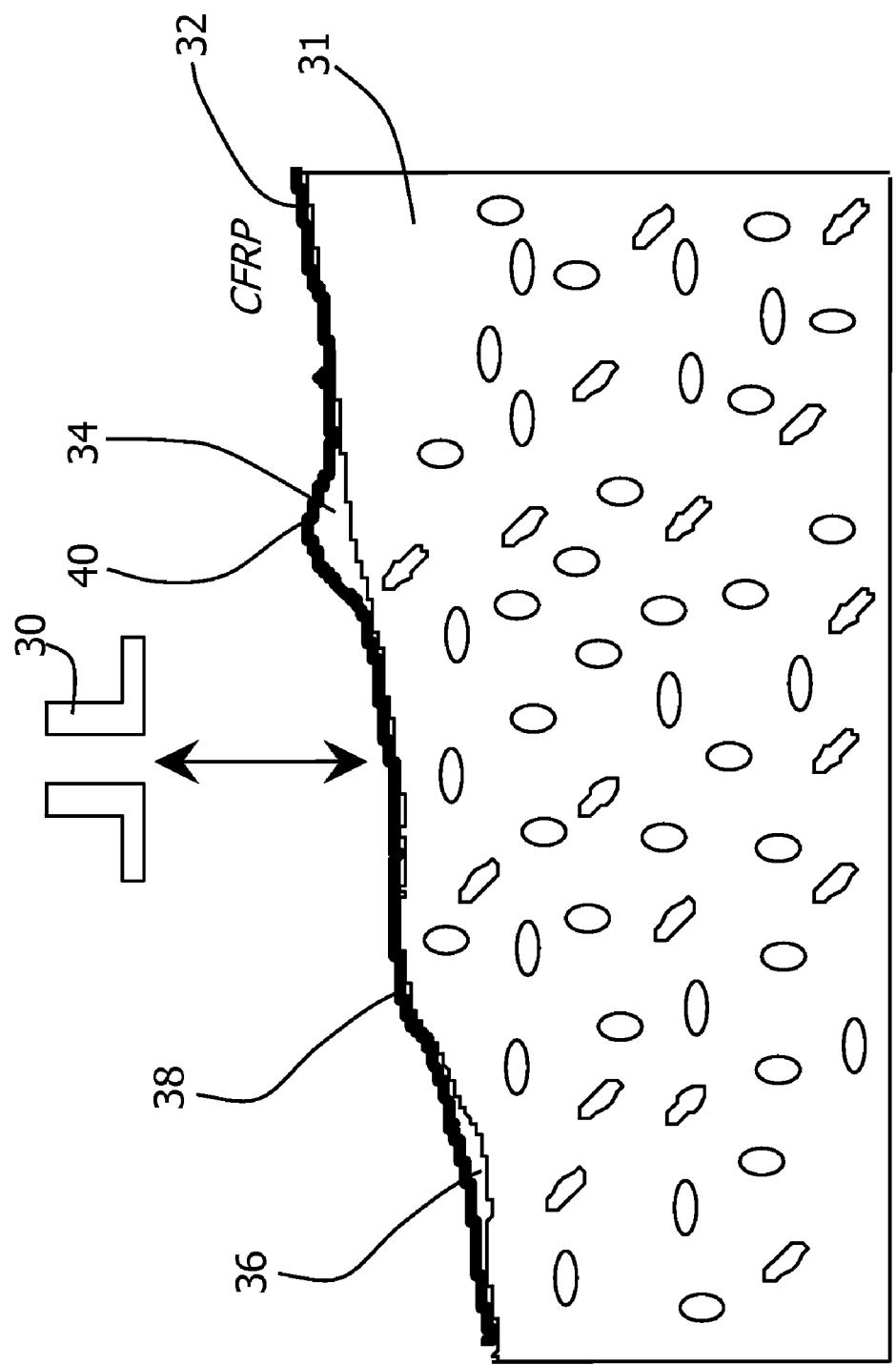
FIG. 4 is a schematic representation of the relationship between the apparatus of the invention and specimen under inspection.

FIG. 4 schematically illustrates the relationship between the probe 30 and the specimen surface 32 (e.g., CFRP) on substrate 31 (e.g., concrete containing aggregate). This depicts issues of surface roughness and surface tilt which the present invention has been designed to address. There is some surface roughness and bulging at 40 associated with disbond 34. Other surface roughness such as at 38 is not associated with any disbond or other defect. Thin disbond 36 does not have any significant surface roughness. In particular, surface roughness and surface tilt manifest themselves as differences in standoff distance. With such differences, there can be inconsistency and uncertainty as to whether the display signal and therefore the display are reflecting subsurface defects or acceptable surface conditions. So that differences in the ultimate display signal reflect defects—disbond and delamination—and not differences in standoff distance, this invention employs the compensation circuit to eliminate the effects of standoff distance on the display signal.

Figure 5:
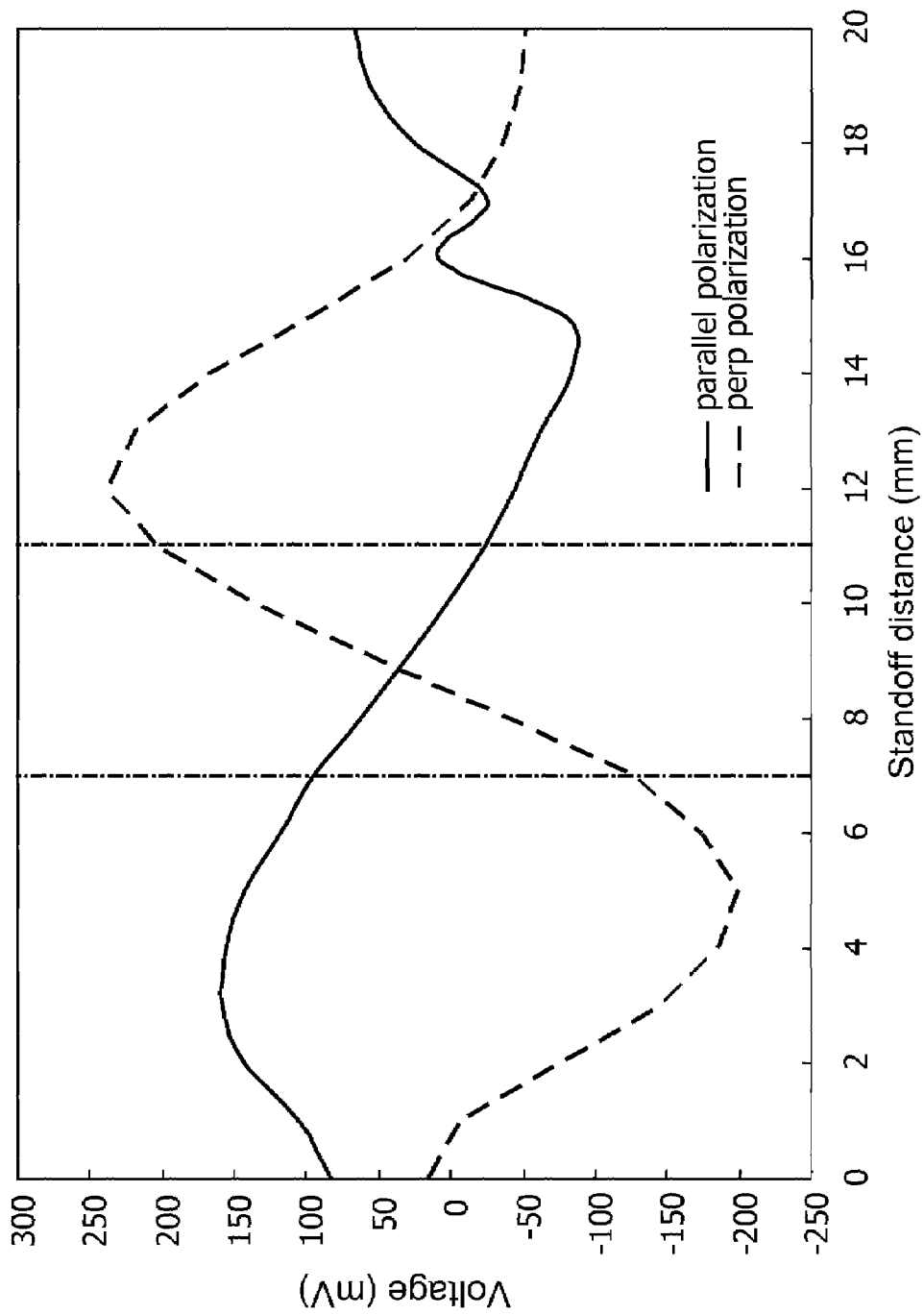
FIGS. 5 and 6 are graphical representations of standoff distance v. voltage.
Figure 6:
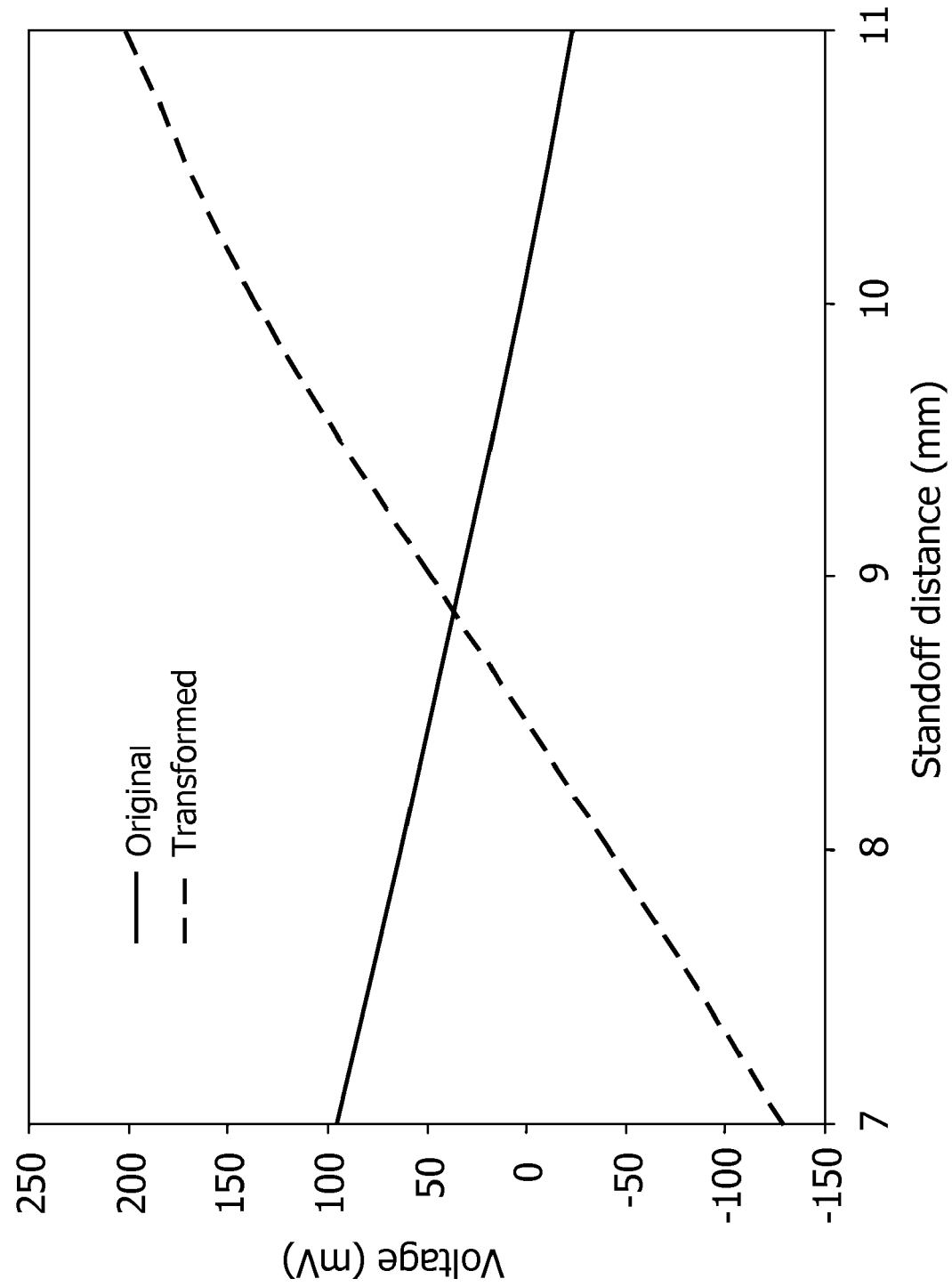

In particular, the parallel-polarized signal is used to achieve effective removal of the influence of standoff distance variations from the perpendicular polarization data/image. The dependency of the output voltages, corresponding to the two orthogonally polarized reflected signals, on standoff distance were measured and analyzed for several CFRP-strengthened cement-based structures leading to the design of the compensation circuit. FIG. 5 shows the typical dependency of the measured output voltages on standoff distance for an irradiated area of CFRP-concrete sample without disbond. As expected and can be seen from FIG. 5, the output voltages do not follow a monotonic change as a function of increasing standoff distance. However, the results show in FIG. 5 that for the standoff distance range of 7 mm-11 mm, both curves are fairly linear. This is important since in this range the parallel polarization output voltage can be used to determine the value of standoff distance and its variation. Subsequently, when operating in this region the influence of standoff distance variation can be measured and removed from the perpendicular polarization data/image using a relatively simple compensation circuit. The compensation circuit first transforms the linear region of the curve for the parallel polarization data to match the corresponding linear region of the curve for the perpendicular polarization, as shown in FIG. 6. This transformation is performed using a polynomial equation which for the linear region in FIG. 6 is:

$$V_{tr} = 0.0045 V_{par}^3 + 0.3786 V_{par}^2 + 13.6093 V_{par} \quad (1)$$

where $V_{tr}$ and $V_{par}$ are transformed voltage and voltage corresponding to signal with parallel polarization, respectively.

The compensated voltage $V_{comp}$ is the difference between the voltage corresponding to the signal of perpendicular polarization $V_{rperp}$ and $V_{tr}$:

$$V_{comp} = V_{rperp} - V_{tr} \quad (2)$$

Subsequently, the transformed data is subtracted from the data corresponding to the perpendicular polarization and in doing so removes the contribution of the reflected signal from the surface of the sample (i.e., change in standoff distance). Then, once a scan is conducted at a standoff distance within the range of 7 mm-11 mm (standoff distance of about 8 mm was used here), the influence of the standoff distance variation from the data corresponding to the perpendicular polarization will be automatically removed and a compensated image of the sample which primarily indicates the presence of a disbond or other defect such as damage of concrete under CFRP, is generated. As a result, the system simultaneously generates three images of the defect and in real time; namely, two at orthogonal polarizations and one (compensated image) after the influence of the undesired standoff distance variation is removed and only information about disbond or other defect such as damage of concrete under CFRP is preserved. Consequently, the invention is capable of i) detection and evaluation of different types of defects such as disbonds and damages of concrete, in structures and ii) reduction of the time required for data processing to produce a meaningful image due to an automatic removal of undesired yet invariably present influence of standoff distance variation. In this way the invention achieves non-contact testing of physical characteristics of composite structures with removal of influence of standoff distance variation that may be smaller than the irradiated area. This is in contrast to the device in U.S. Pat. No. 6,462,561 which assimilates microwave signals with potentiometer contact measurements and is ineffective when the specimen has local surface variation that may be smaller in spatial extent than irradiated area and in contrast to the alternative system in U.S. Pat. No. 5,886,534 which is ineffective when the specimen has surface roughness/bulging that may be smaller in spatial extent than the separation between the two sensing locations (about 3 inches) or when defects are not oriented.

The method of the invention is performed in near-field mode rather than far-field mode. In a preferred embodiment at X-band (8.2-12.4 GHz) the specimen is positioned in the near-field region of the probe, which is that region in which the electric properties of electromagnetic signals transmitted by the probe change as a function of directions transverse to the direction of propagation as well as a function of the direction of propagation, e.g., between about 7 and about 11 mm from the aperture of the probe, consistent with the standoff distance discussed above. With near-field microwave measurements, wave both magnitude and phase are sensitive to changes associated with variations of physical characteristics of composite structures.

The invention is further illustrated by the following non-limiting examples:

EXAMPLE 1

CFRP laminates were adhered to several cement-based samples after curing using a manual lay-up method. During the lay-up process, several intentionally disbonded regions were produced in each sample. Specimen #1 was a 380 mm by 520 mm by 90 mm mortar slab adhered with a CFRP laminate. A 60 mm by 80 mm rectangular disbonded region was produced by inserting a thin sheet of foam between the CFRP laminate and the mortar substrate. Specimen #2 was a 380 mm by 520 mm by 78 mm mortar slab with several disbonded regions produced in it by injecting air between the CFRP laminate and the mortar substrate (i.e., creating a thin airgap between CFRP and mortar). The manufactured disbonds varied in size, geometry and thickness, and ranged in area from approximately a few to several squared centimeters. Some of the disbonds also bulged up a bit creating local surface roughness that when scanned would result in standoff distance variation around it.

Figure 7:
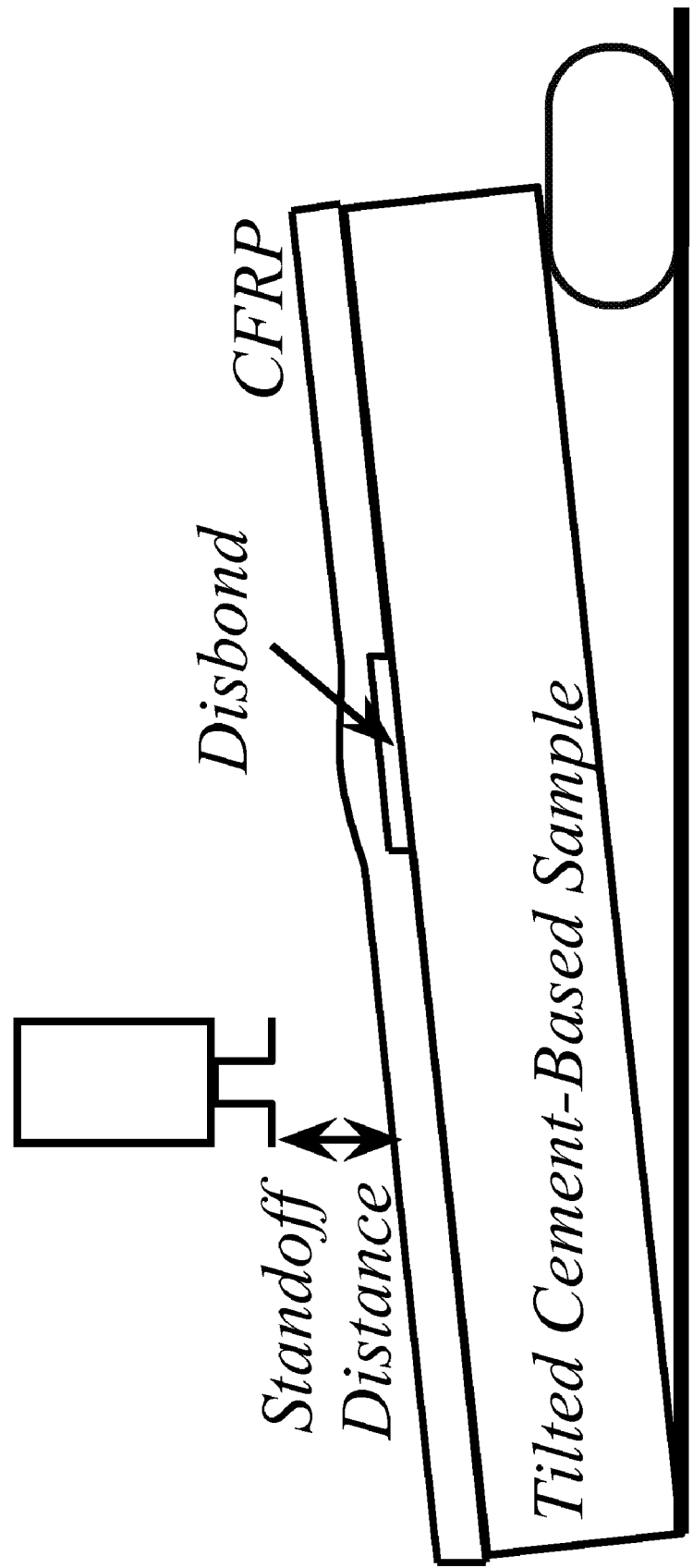
FIG. 7 is a schematic representation of a test performed in accordance with the invention.
Figure 8A:
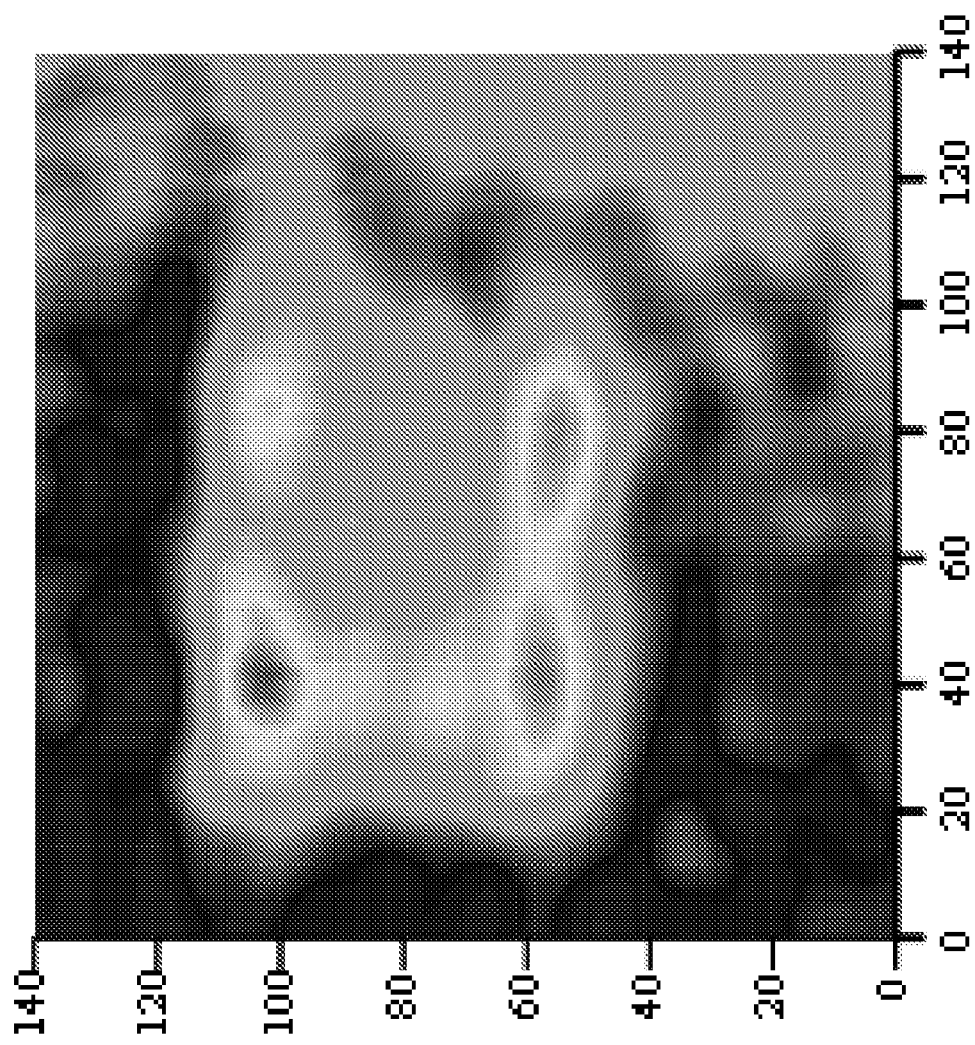
FIGS. 8, 9, 11, and 12 are microwave images generated in accordance with the invention.
Figure 8B:
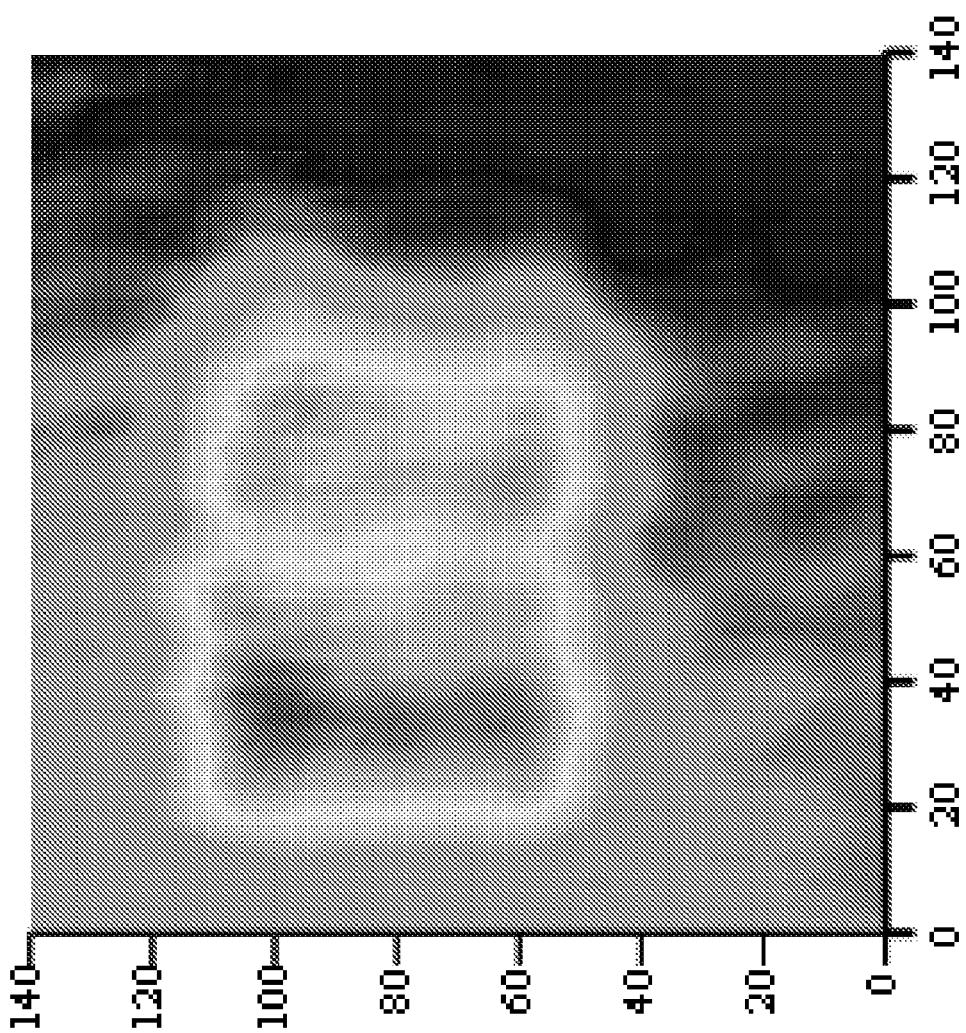
Figure 8C:
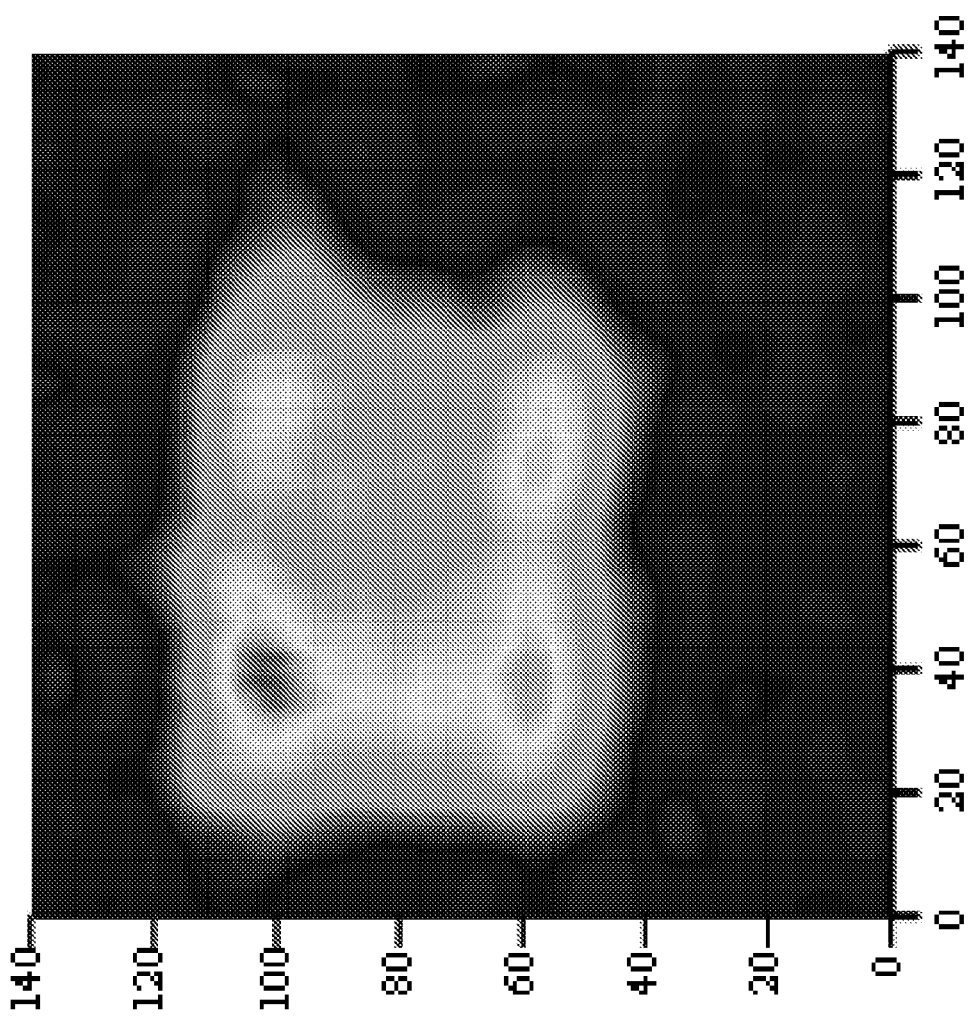

Specimen #1 (380×520 mm surface) was mounted on the apparatus as shown in FIG. 3 with an intentional tilt as shown schematically in FIG. 7 with respect to the probe scan plane to produce relatively severe standoff distance variation. An area of 140 mm by 140 mm, including the 60 by 80 mm disbond area, was raster scanned. Its image was produced by recording the raster output voltages from the two orthogonally polarized ports, normalizing each data matrix with respect to its highest voltage value, and producing a grey scale image. FIG. 8a shows the perpendicular polarization image, FIG. 8b shows the parallel polarization image, and FIG. 8c shows the compensated image, with the dimensions shown in mm. The perpendicular polarization image FIG. 8a, which is influenced by characteristics internal to the specimen as well as by standoff distance, shows lighter features associated with the disbond area in the middle of the display. It also shows lighter features at the area on the right side associated with the more raised aspect of the tilted surface. The parallel polarization image in FIG. 8b, which is influenced primarily by variations in standoff distance, shows contrast between the left side of the image versus the right side of the image associated with the tilt, and contrast in the middle associated with bulging resulting from the disbond. So, both images show a gradual intensity change from left to right representing the intentionally induced standoff distance change over the scanned area due to the specimen tilt, in addition to effects of the disbond. FIG. 8c shows the compensated image in which the effect of standoff distance variation is completely removed from the perpendicularly-polarized image of 8a. FIG. 8c clearly shows the disbanded region and indicates the fact that its thickness is not uniform. Significantly, the area surrounding the disbond is fairly uniform (unlike that in FIG. 8a) indicating the utility of this method and apparatus for effectively eliminating the undesired influence of standoff distance variation from the perpendicularly-polarized image. Furthermore, the dimensions of the disbanded region associated with its image in FIG. 8c correspond well to its actual dimensions.

Figure 9:
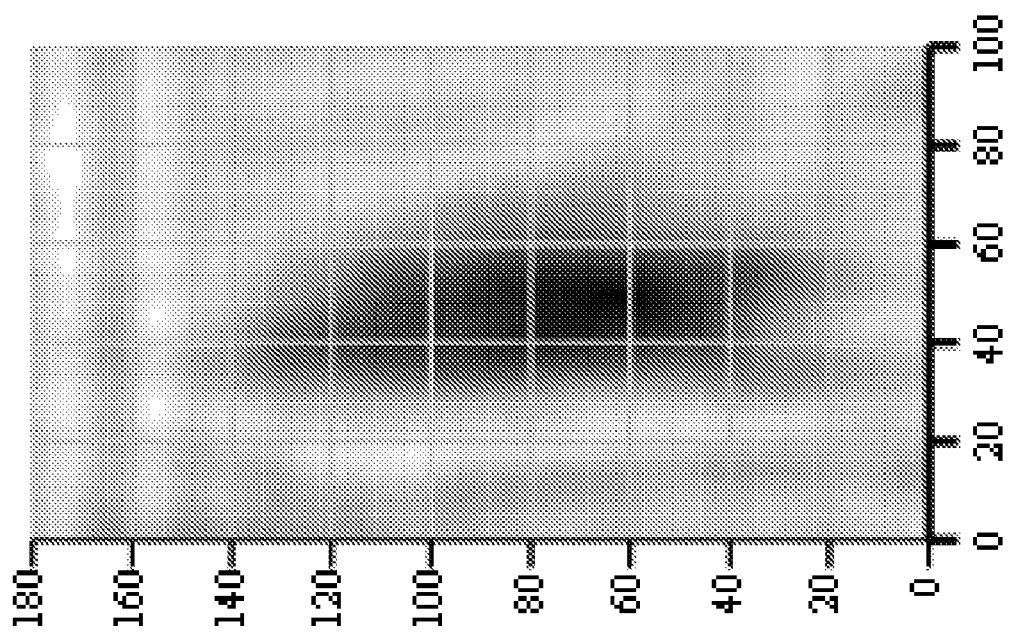
Figure 10:
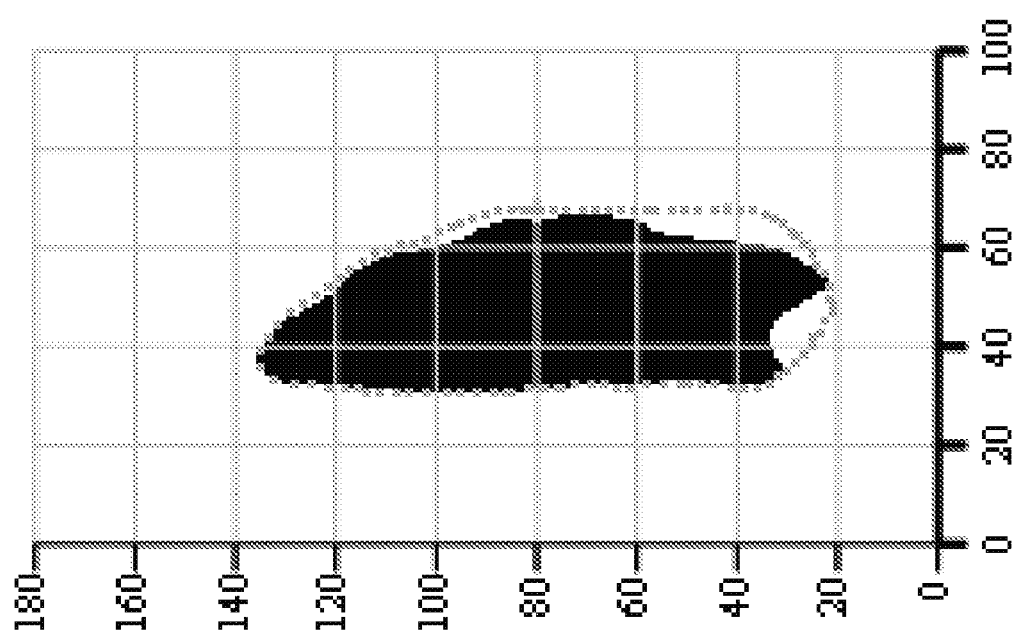
FIG. 10 is an overlay of a tap test onto a microwave test image generated in accordance with this invention.

Images of Specimen #2 containing several disbonds with different sizes and shapes were produced in a manner similar to Example 2. The disbond boundaries indicated by the respective compensated images were compared with the results of physical tap testing, which closely indicates the boundaries of a disbond. The compensated image of one of the disbonds of Specimen #2 is shown in FIG. 9. These results show that the shape of this disbond is complex while its exact boundary is not clear. FIG. 10 shows, in black v. white contrast, the boundaries of this disbond corresponding to the 3-dB intensity level of the image. The dashed line shows these boundaries from tap testing. The results indicate that compensated images of disbonds can provide close estimate of their boundaries. This is an important feature when considering repair of disbanded areas, which is commonly accomplished by injecting epoxy into the disbanded region.

EXAMPLE 2

Figure 11A:
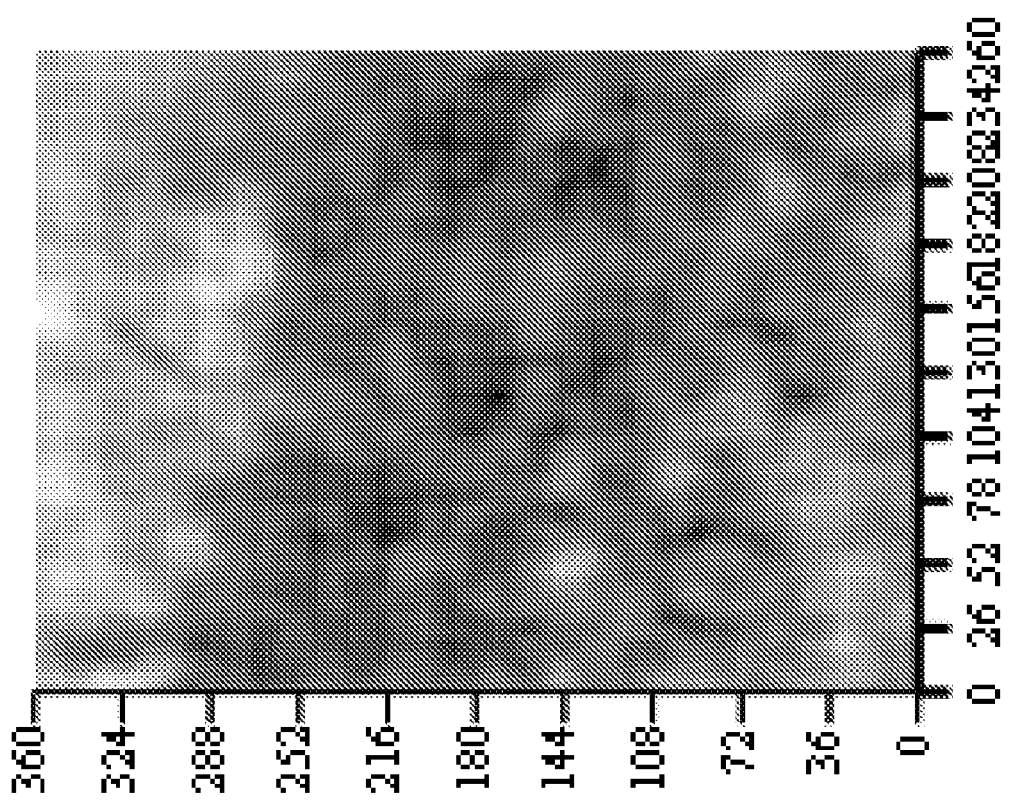
Figure 11B:
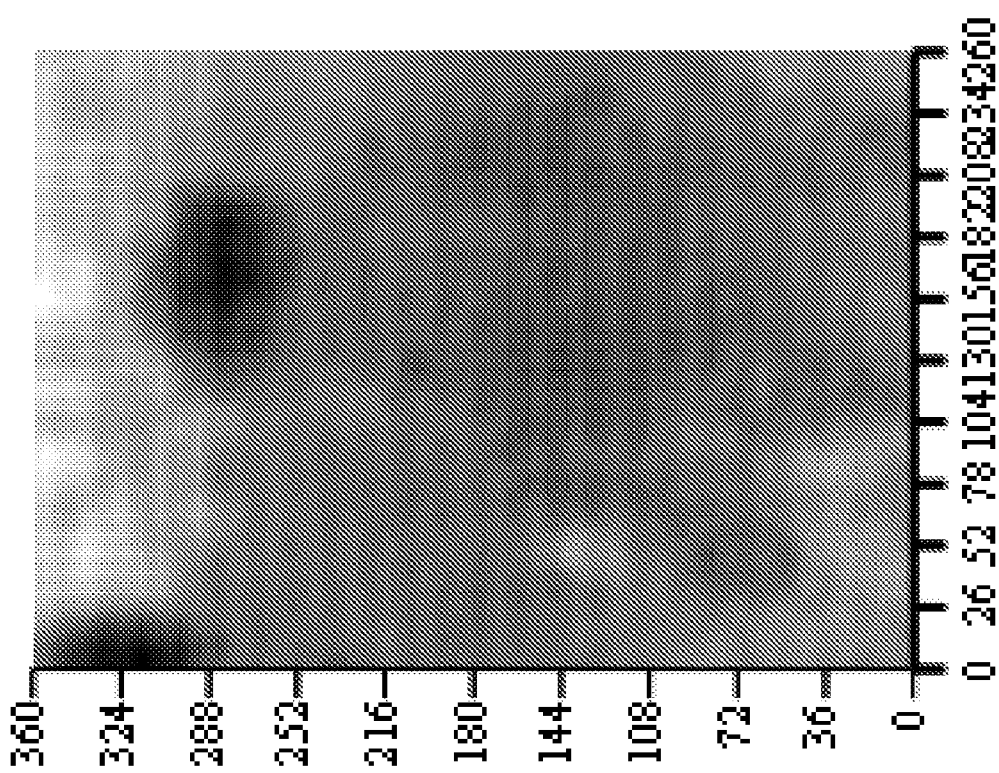
Figure 11C:
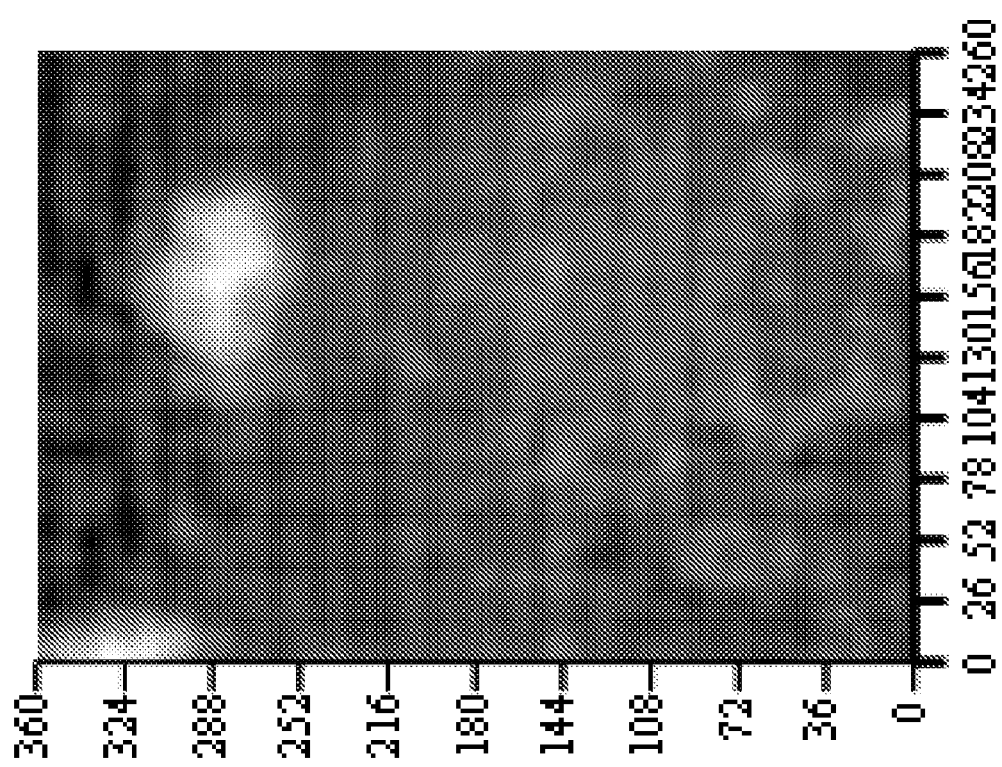
Figure 12A:
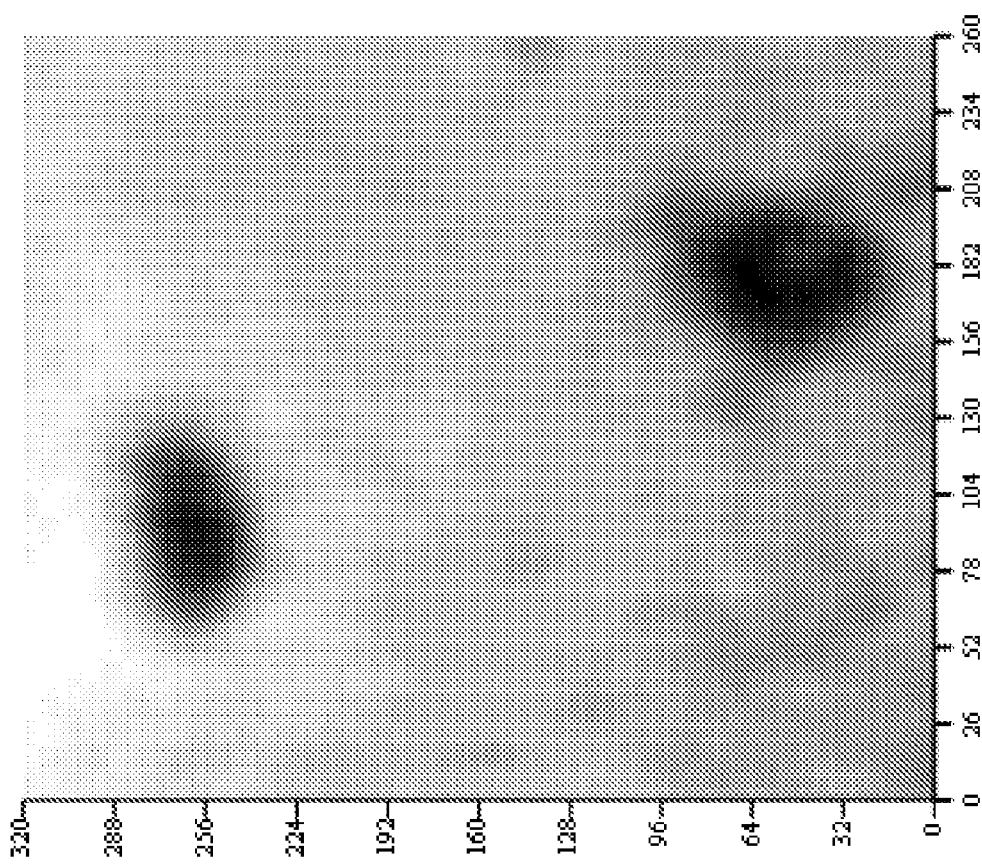
Figure 12B:
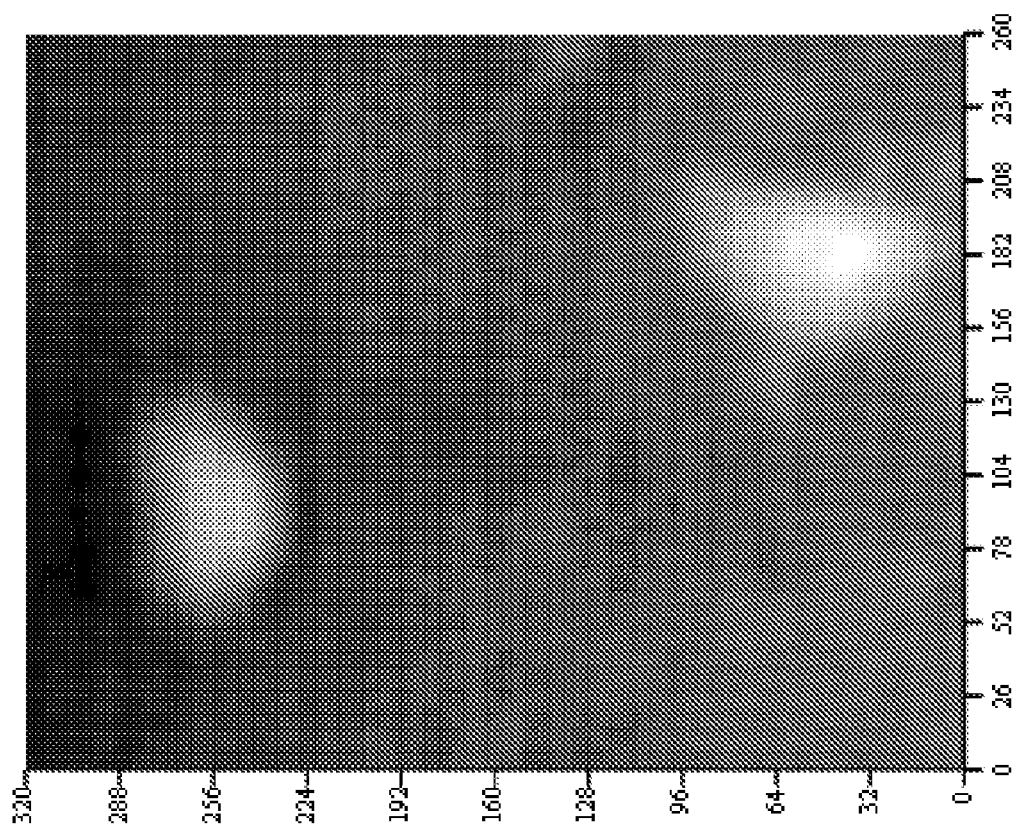
Figure 12C:
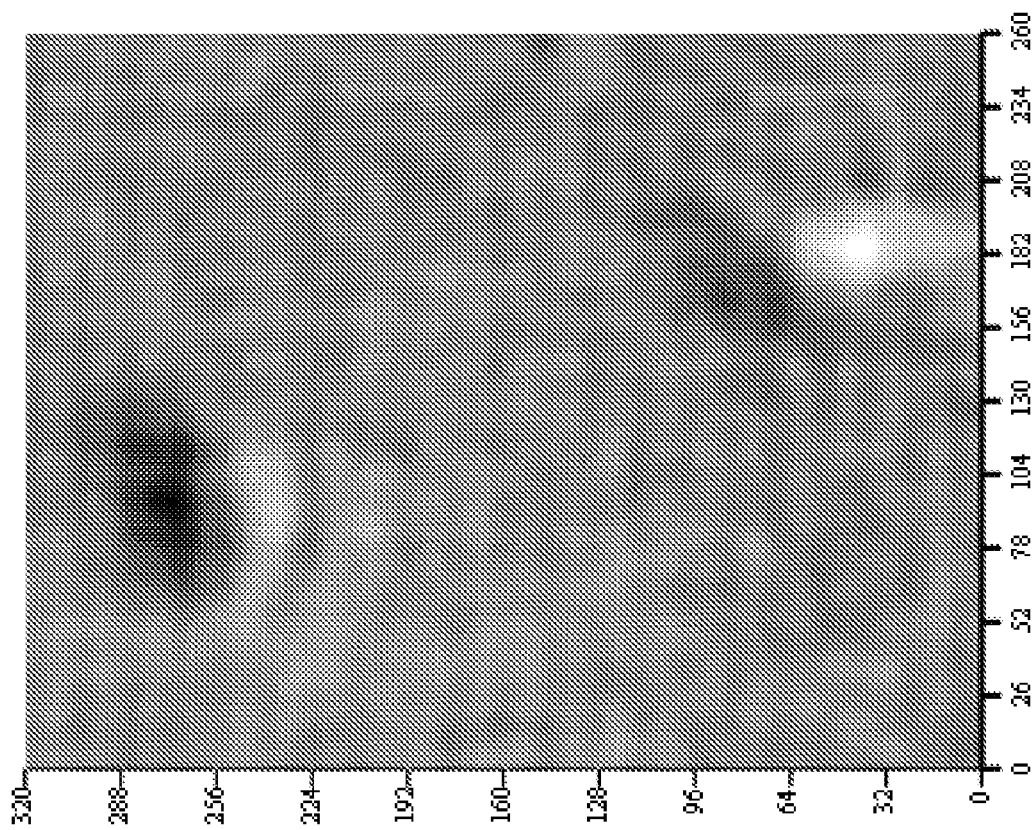

In-field inspection and monitoring of CFRP-strengthened concrete members was conducted on an actual bridge. Disbonds were intentionally introduced into CFRP patches on a bent (transverse bridge member) and on an abutment. FIGS. 11 a-c show the microwave images of a 260 mm by 360 mm scanned area of the bonded CFRP patch on the bent, and FIGS. 12 a-c show microwave images of a 260 mm by 320 mm scanned area of the bonded CFRP patch on the abutment. The figures show a) perpendicular polarized images, b) parallel polarized images, and c) compensated images, respectively. The results show that the image 11a from the bent patch at perpendicular polarization is more non-uniform than the image 12a of the abutment patch. This is due to the fact that the disbonds produced in the bent were thinner than the disbonds produced in the abutment, and the influence of standoff distance variation was also relatively more significant. The dark indications in the perpendicular polarization image in FIG. 12a represent two different disbonds. The indications of the slight surface bulging due to the presence of air between CFRP and concrete are also clearly visible in the image for parallel polarization (bright indications in FIG. 12b). The compensated images (11c, 12c) clearly indicate the disbonds as well as the local non-uniformity associated with them. The locations and sizes of the detected disbonds, indicated by these compensated images, agrees well with their locations and sizes on the bonded CFRP patches and were corroborated by tap testing.

The foregoing illustrates detection and evaluation of disbonds between CFRP laminates and concrete. Other anomalies including delamination and damage to concrete under CFRP laminates similarly produce images of different color and/or intensity at the location of the anomaly, because these anomalies similarly affect phase and/or magnitude changes in reflected electromagnetic signals.

Figure 13:
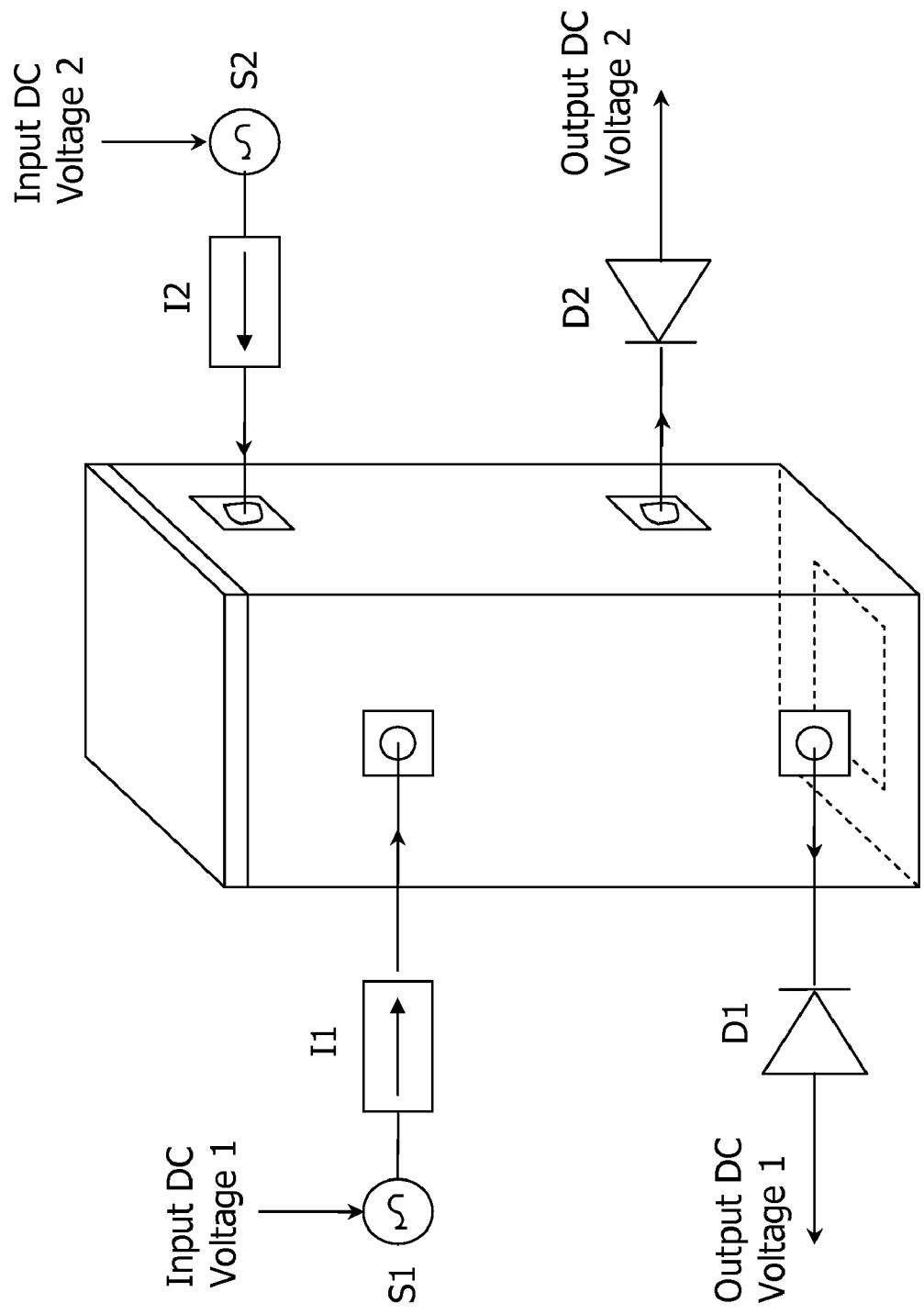
FIGS. 13, 14, and 15 are schematic representations of alternative versions of the dual-polarized square waveguide and different accompanying circuitries.

Different circuits sensitive to phase and/or magnitude can be used to produce DC voltages. For example, FIG. 13 shows a probe with microwave circuits which are sensitive to both phase and magnitude. They include detectors D1 and D2, and in comparison to the circuit in FIG. 2, they omit mixers and do not use directional couplers providing an external reference signal from the oscillators. To simplify the dual-polarized probe its 2-port versions can be used. The various aspects including a first microwave circuit for microwave signals with polarization perpendicular to the orientation of the relevant feature of the specimen, second microwave circuit for microwave signals with polarization parallel to the orientation of the relevant feature of the specimen, housing, opening, microwave source (S1, S2), and isolator (I1, I2) are the same as described above in connection with FIG. 2.

Figure 14:
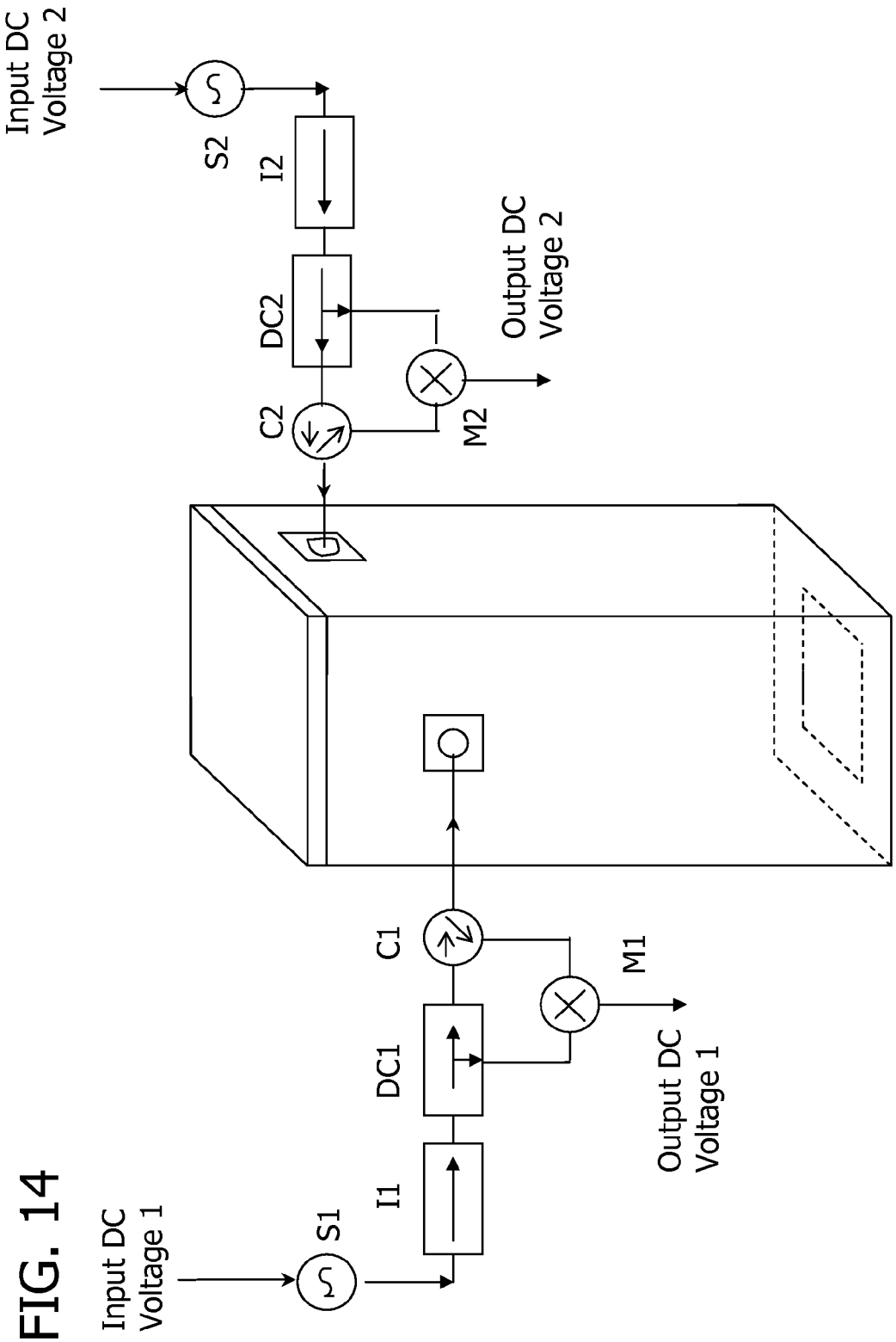
Figure 15:
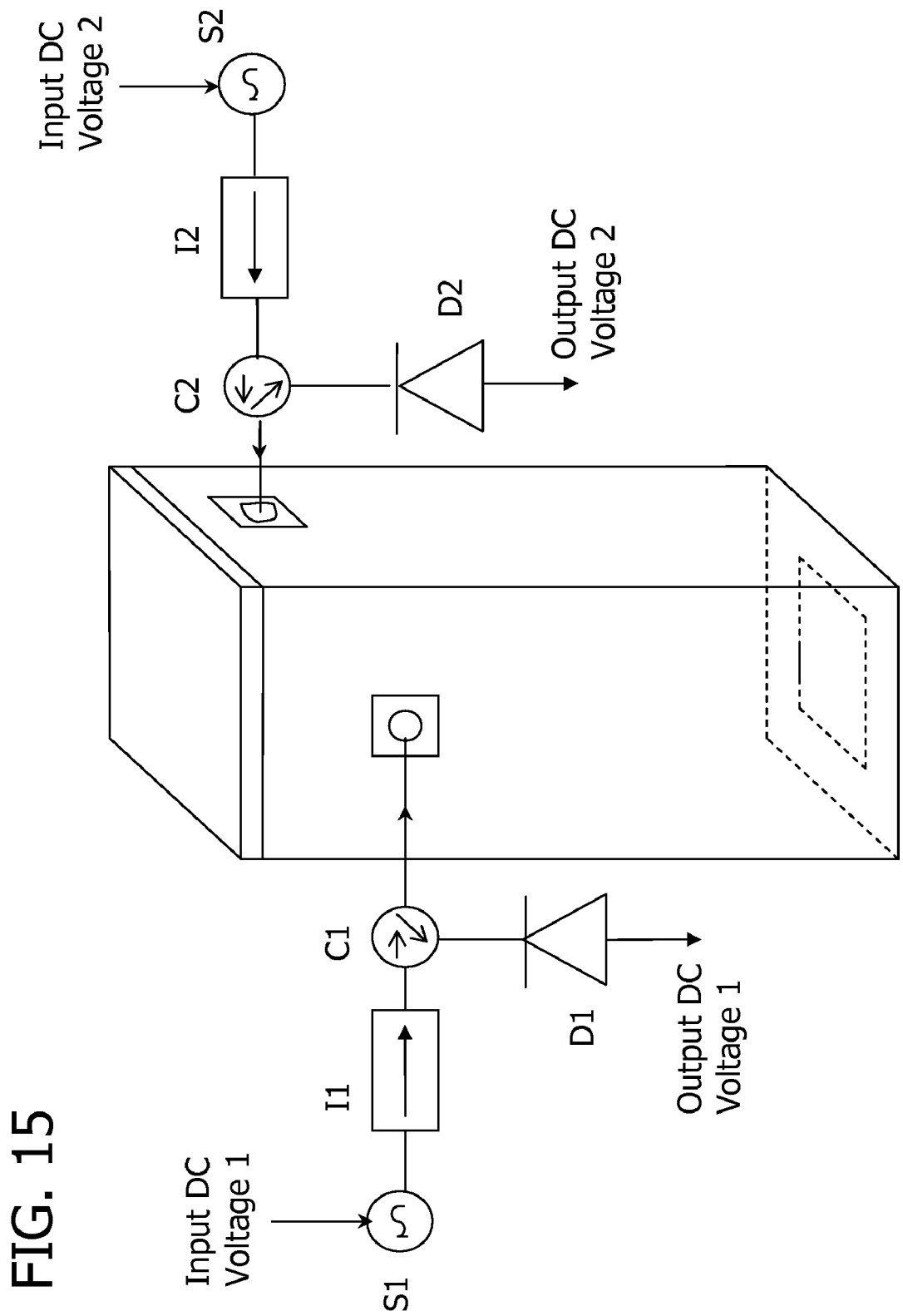

FIG. 14 shows a 2-port dual-polarized probe with microwave circuits including circulators C1, C2 and mixers M1, M2. The simplest 2-port version of the probe with detectors D1 and D2 is shown in FIG. 15. The various aspects including a first microwave circuit for microwave signals with polarization perpendicular to the orientation of the relevant feature of the specimen, second microwave circuit for microwave signals with polarization parallel to the orientation of the relevant feature of the specimen, housing, opening, microwave source (S1, S2), isolator (I1, I2), and direct coupler (DC1, DC2) are the same as described above in connection with FIG. 2.

The apparatuses in FIGS. 2 and 13 comprise four ports, namely, separate ports for the transmitted signal of the first polarization orientation, the reflected signal of the first polarization orientation, the transmitted signal of the second polarization orientation, and the reflected signal of the second polarization orientation. In contrast, the apparatuses of FIGS. 14 and 15 comprise two ports, with a shared port for the transmitted and reflected signal of the first polarization orientation and a shared port for the transmitted and reflected signal of the second polarization orientation.

When introducing elements of the present invention or the preferred embodiment(s) thereof, the articles "a," "an," "the," and "said" are intended to mean that there are one or more of the elements and numbers such as "two" mean there are at least two of the elements unless stated otherwise. For example, that the foregoing description and following claims refer to "an" anomaly means that there are one or more such anomalies and does not exclude more than one anomaly. The terms "comprising," "including," and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense. The scope of invention is defined by the appended claims and modifications to the embodiments above may be made that do not depart from the scope of the invention.

What is claimed is:

1. A method for detecting an anomaly in a composite material comprising:
   directing two transmitted electromagnetic wave signals orthogonally polarized with respect to each other from a square waveguide probe to the composite material, wherein the probe and composite material are positioned for evaluation of the composite material in near-field of the probe;
   wherein the respective transmitted electromagnetic wave signals are issued simultaneously by two distinct transmitters through a common square opening of said square waveguide probe;
   receiving two reflected signals corresponding to said two transmitted orthogonally polarized signals; and
   issuing information about the composite material developed as a function of phase differences between the transmitted and the reflected signals.

2. The method of claim 1 wherein the two transmitted electromagnetic signals irradiate the composite material at the same location.

3. The method of claim 1 further comprising:
   directing the reflected signals having been received to two detectors which generate two detector output voltages corresponding to the reflected signals; and
   applying the two detector output voltages to a compensator circuit to compensate for changes in standoff distance between the probe and the composite material, wherein the compensator circuit generates a compensated voltage signal as a function of a detector output voltage corresponding to the reflected signal with the perpendicular polarization and a detector output voltage corresponding to the reflected signal with the parallel polarization; and
   issuing said information about the composite material on the basis of the compensated voltage signal.

4. The method of claim 1 wherein
   the composite material comprises elongate elements in a matrix of dielectric material;
   the elongate elements are aligned in a common direction and reflect parallel-polarized electromagnetic wave signals; and
   the two transmitted electromagnetic wave signals which are orthogonally polarized with respect to each other comprise a first transmitted signal which electric field polarization vector is parallel to a preferred orientation of the elongate elements in the composite material and a second transmitted signal which electric field polarization vector is orthogonal to the preferred orientation of the elongate elements in the composite material.

5. The method of claim 1 wherein the two reflected signals comprise a first reflected signal generated by reflection of the first transmitted signal from a location beneath the surface of the material or behind the material, and a second reflected signal generated by reflection of the second transmitted signal from the surface of the material.

6. The method of claim 1 wherein the probe comprises a first transmitter for parallel-polarized signals and a second transmitter for perpendicular-polarized signals.

7. The method of claim 1 further comprising:
   directing the reflected signals having been received to two detectors which generate two detector output voltages corresponding to the reflected signals; and
   applying the two detector output voltages to a compensator circuit which generates a voltage signal providing said information about the composite material;
   wherein:
   the two transmitted electromagnetic signals irradiate the composite material at the same location;
   the composite material comprises elongate elements in a matrix of dielectric material and the elongate elements are aligned in a common direction and reflect parallel-polarized electromagnetic wave signals;
   the two transmitted electromagnetic wave signals which are orthogonally polarized with respect to each other comprise a first transmitted signal which electric field polarization vector is parallel to a preferred orientation of the elongate elements in the composite material and a second transmitted signal which electric field polarization vector is orthogonal to the preferred orientation of the elongate elements in the composite material;
   the two reflected signals comprise a first reflected signal generated by reflection of the first transmitted signal from a location beneath the surface of the material or behind the material, and a second reflected signal generated by reflection of the second transmitted signal from the surface of the material;
   the probe is an open-ended square waveguide probe comprising a first transmitter for parallel-polarized signals and a second transmitter for perpendicular-polarized signals.

8. The method of claim 1 wherein the composite material comprises carbon fiber reinforced polymer material laminated onto concrete.

9. The method of claim 1 wherein the probe is positioned between about 7 and about 11 mm from the composite material.

10. The method of claim 1 wherein the two transmitted electromagnetic wave signals are issued at respective frequencies different from each other.

11. The method of claim 7 wherein the two transmitted electromagnetic wave signals are issued at respective frequencies different from each other.

12. The method of claim 7 wherein the composite material comprises carbon fiber reinforced polymer material laminated onto concrete.

13. The method of claim 7 wherein the probe is positioned between about 7 and about 11 mm from the composite material.

14. A method for detecting an anomaly in a composite material comprising:
   directing two transmitted electromagnetic wave signals from a square waveguide probe to the composite material, wherein the two transmitted electromagnetic wave signals are orthogonally polarized with respect to each other and are issued at respective frequencies different from each other and wherein the probe is an open-ended square waveguide probe;
wherein the respective transmitted electromagnetic wave signals are issued simultaneously by two distinct transmitters through a common square opening of said open-ended square waveguide probe;
receiving two reflected signals corresponding to said two transmitted electromagnetic wave signals which are orthogonally polarized; and
issuing information about the composite material developed as a function of phase differences between the transmitted and the reflected signals.

15. The method of claim 14 wherein
the composite material comprises elongate elements in a matrix of dielectric material;
the elongate elements are aligned in a common direction and reflect parallel-polarized electromagnetic wave signals; and
the two transmitted electromagnetic wave signals which are orthogonally polarized with respect to each other comprise a first transmitted signal which electric field polarization vector is parallel to a preferred orientation of the elongate elements in the composite material and a second transmitted signal which electric field polarization vector is orthogonal to the preferred orientation of the elongate elements in the composite material.

16. The method of claim 14 wherein said frequencies differ by about 2 GHz.

17. A method for detecting an anomaly in a carbon fiber reinforced polymer material adhered to a concrete substrate comprising:
directing two transmitted electromagnetic wave signals from a square waveguide probe to the carbon fiber reinforced polymer material, wherein a first of the two transmitted electromagnetic wave signals is polarized parallel to the preferred orientation of carbon fibers in the carbon fiber reinforced polymer material, and a second of the two transmitted electromagnetic wave signals is polarized orthogonally with respect to the first of the signals;
wherein the respective transmitted electromagnetic wave signals are issued simultaneously by two distinct transmitters through a common square opening of said square waveguide probe;
receiving two reflected signals corresponding to said two transmitted electromagnetic signals which are orthogonally polarized; and
issuing information about the composite material developed as a function of the two reflected signals.

18. An apparatus for detecting an anomaly in a composite material comprising fibers within a composite dielectric material, the apparatus comprising:
an open-ended square waveguide probe comprising a first transmitter for transmitting electromagnetic signals with a first electric field polarization vector orientation at the composite material located in near-field region of the probe, and a second transmitter for transmitting electromagnetic wave signals with a second electric field polarization vector orientation at the composite material, wherein the second electric field polarization vector orientation is orthogonal to the first electric field polarization vector orientation;
wherein the respective transmitted electromagnetic wave signals are issued simultaneously by said two distinct transmitters through a common square opening of said square open-ended waveguide probe;
the probe further comprising a first receiver for receiving reflected signals of the first polarization orientation, and a second receiver for receiving reflected signals of the second polarization orientation; and
a conditioning circuit for translating the reflected signals to information about the composite material.

19. The apparatus of claim 18 wherein the probe comprises a housing having a shared port for the transmitted and reflected signal of the first polarization orientation and a shared port for the transmitted and reflected signal of the second polarization orientation.

20. The apparatus of claim 18 wherein the probe comprises a housing having separate ports for the transmitted signal of the first polarization orientation, the reflected signal of the first polarization orientation, the transmitted signal of the second polarization orientation, and the reflected signal of the second polarization orientation.

21. The apparatus of claim 18 wherein the apparatus detects differences in phase and magnitude between received and transmitted electromagnetic signals.

22. The apparatus of claim 18 further comprising a first mixer for combining transmitted and reflected signals of the first polarization orientation, and a second mixer for combining transmitted and reflected signals of the second polarization orientation, wherein the first and second mixer thereby produce DC output voltages proportional to phase differences between the transmitted and the received signals.

* * * * *